(12) United States Patent
Zecchino et al.

(10) Patent No.: US 7,682,620 B2
(45) Date of Patent: Mar. 23, 2010

(54) GELLED AQUEOUS COSMETIC COMPOSITIONS

(75) Inventors: Jules Zecchino, Closter, NJ (US);
Michelle Matathia, Syosset, NY (US);
E. Althea Knight, Teaneck, NJ (US);
James T. Harrison, Forest Hills, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/995,358

(22) Filed: Nov. 26, 2001

(65) Prior Publication Data

US 2002/0058055 A1    May 16, 2002

Related U.S. Application Data

(63) Continuation of application No. 09/510,756, filed on Feb. 22, 2000, now abandoned.

(51) Int. Cl.
*A61K 8/04* (2006.01)
*A61K 9/14* (2006.01)

(52) U.S. Cl. ...................... 424/401; 424/486

(58) Field of Classification Search ................ 424/449, 424/401, 486, 484
See application file for complete search history.

(56) References Cited

U.S. PATENT DOCUMENTS

| | | | |
|---|---|---|---|
| 4,184,978 A * | 1/1980 | France et al. | ................ 516/29 |
| 4,999,198 A | 3/1991 | Barnett et al. | |
| 5,667,789 A * | 9/1997 | Collin et al. | ................ 424/401 |
| 6,224,888 B1 * | 5/2001 | Vatter et al. | ................ 424/401 |
| 6,294,186 B1 * | 9/2001 | Beerse et al. | ................ 424/405 |

FOREIGN PATENT DOCUMENTS

| WO | WO 97/32559 | * | 9/1997 |
|---|---|---|---|
| WO | WO 9732559 | * | 9/1997 |

OTHER PUBLICATIONS

Clatiant Product Brochure.*
Clariant Product Brochure, Feb. 1999.*
Clariant Product Brochure Jan. 1999.*
PCT International Search Report; International Application No. PCT/US01/05422; Completion Date: Jun. 7, 2001; Date of Mailing: Jun. 18, 2001.

* cited by examiner

*Primary Examiner*—Blessing M Fubara
(74) *Attorney, Agent, or Firm*—Cynthia R. Miller

(57) ABSTRACT

The invention relates to cosmetic or pharmaceutical composition comprising an oil-containing biliquid foam dispersed in a salt-containing aqueous phase, in which the aqueous phase, having a pH of less than about 7, is gelled by a polymeric sulfonic acid. A particularly preferred gellant is ammonium poly(acryldimethyltauramide-co-vinylformamide). Unlike many other types of gels, these gels are stable at an acid pH in the presence of substantial amounts of electrolytes, and therefore are useful in delivering acidic active components.

17 Claims, No Drawings

GELLED AQUEOUS COSMETIC COMPOSITIONS

This application is a continuation of Ser. No. 09/510,756, filed Feb. 22, 2000, now abandoned.

FIELD OF THE INVENTION

The invention relates to cosmetic compositions. More specifically, the invention relates to cosmetic compositions containing biliquid foams.

BACKGROUND OF THE INVENTION

Delivery of unique skin treatment products always presents a problem to the formulator. Many of the most useful skin-therapeutic agents are biologically active, and are therefore not useful if there activity is compromised in any way. This means the formulator must choose a delivery vehicle that will be compatible with the active, not causing a degradation of the compound's activity. Maintaining the stability of the active components of a formulation may however sometimes be at odds with the design of a cosmetically acceptable vehicle. Although the modern consumer is more demanding with respect to getting a therapeutic effect with her cosmetics, she ordinarily will not at the same time sacrifice the aesthetics of the product to obtain this. Thus, the formulator is frequently presented with the dilemma of how to provide the maximum therapeutic effect in a vehicle that is cosmetically elegant, yet not necessarily innately compatible with the desired active agent.

This problem is seen particularly in the preparation of gel-type compositions. A gel vehicle is particularly popular now, for a number of reasons: in its most desirable incarnation, a gel, specifically a water-based gel, is cooling, gentle, and non-greasy on the skin. However, achieving maximum efficacy of incorporated actives while fully retaining aesthetics of the vehicle presents substantial difficulty in gel formulation. Incorporation of other useful cosmetic ingredients can cause a loss of clarity, rendering the gel cloudy and less attractive. Similarly, many types of actives can cause a disruption of the gel structure, which can cause instability of the product as a whole, and/or result in a product that has an unacceptable feel when applied to the skin. This problem is particularly difficult when the active components comprise one or more acids, which are frequently present in the composition as electrolytes, as electrolytes can seriously interfere with the maintenance of a stable, clear gel product. A particularly desirable gel vehicle is one in which a biliquid foam is dispersed, such as is described in WO 97/32559. A biliquid foam is advantageous because it permits the incorporation of a relatively large quantity of oil, and oil soluble actives, into an aqueous phase with the use of a very small amount of surfactant. However, the gelling of the aqueous vehicle containing the biliquid foam is quite difficult in the presence of electrolytes, particularly when the pH is acidic.

There thus continues to be a need for improved aqueous gel formulations that can be used to deliver the necessary therapeutic agents while at the same time retain stability and the elegant texture consumers expect from a gel product. The present invention provides such a product.

SUMMARY OF THE INVENTION

The invention provides a cosmetic or pharmaceutical composition comprising a salt-containing gelled aqueous phase in which a biliquid foam is dispersed, the aqueous phase having a pH less than about 7, and being gelled by a polymeric sulfonic acid. Unlike other gelling agents for aqueous systems, this gelling agent can be used in the presence of substantial amounts of salts in an aqueous phase, without any harmful effects on the texture of the gel. The aqueous systems of the invention are therefore useful in delivering salt or electrolytic active materials to the skin in a convenient and aesthetically pleasing manner.

DETAILED DESCRIPTION OF THE INVENTION

The gelling agent of the invention is a polymeric sulfonic acid. Most preferably, the polymer is an ammonium poly (acryldimethyltauramide-co-vinylformamide), also referred to as AMPS/VIFA copolymer, available commercially from Clariant Corporation, Charlotte, N.C. under the name trade name Aristoflex AVC®. The polymer is known as a gelling agent. However, unexpectedly, the gellant is substantially unaffected by the presence of salts in the aqueous phase of the composition, thereby producing a smooth, non-pilling gel.

The gellant can be used to gel any type of cosmetic or pharmaceutical system containing a water phase having salts incorporated therein. Thus, the compositions of the invention may be entirely aqueous, or they may be oil and water emulsions or dispersions. The effective amount of gellant used may be from about 0.01% to about 10% by weight of the total composition, more preferably from about 1 to about 5%, the concentration being dependent upon the desired viscosity of the resulting gel. The aqueous phase can further comprise from about 1 to about 10% by weight of one or more salts, preferably skin active agents, such as salts of alpha and beta hydroxy acids, and related compounds, for example, metal salts of lactic acid, malic acid, glycolic acid, lactobionic and salicylic acid. These neutralized forms of the free acids are widely used in cosmetics, because they cause substantially less irritation to the skin than the free acids from which they are derived. However, it has heretofore been virtually impossible to provide a stable aqueous gel, at a pH below 7, in their presence, because the salts interferes when standard aqueous gelling agents, such as Carbopol or cellulose derivatives are used. The use of the polymeric sulfonic acid permits the preparation of such gels, which spread smoothly on the skin and thus can deliver the desired active components effectively and elegantly.

The polymer is used as a gellant in an aqueous dispersion of a biliquid foam. Biliquid foams are dispersions of oil droplets in aqueous media that are stabilized by thin films that contain small quantities of surfactants. In general terms, these are prepared, for example, by blowing air through a water and surfactant mixture to create a foam, and then mixing in the desired oil. Biliquid foams are particularly useful because they permit the incorporation of a fairly large amount of oil, particularly silicone oils, into water, with the use of a fairly small amount of surfactants. Unlike an emulsion, these foams are generally unstable, or insufficiently stable to be very useful in most cosmetic formulations, since the foam tends to break at the air-water interface, depositing an undesirable layer of oil on the surface. Improved compositions containing biliquid foams are described in WO 97/32559, the contents of which are incorporated herein by reference. In this publication, biliquid foams are incorporated as dispersions in aqueous gels, which stabilizes the foam sufficiently to permit its use in a variety of cosmetic products, such as shampoos, shower gels, moisturizers, cleansers, and the like. The gellants recommended for use with the aqueous gels include alginates, guar gum, xanthan gum, cellulose derivatives, bentonites, carbomers, and glyceryl polymethacrylates. However, although these gellants can perform adequately in formulations with high (i.e., >7) pH, it has been observed that a wide range of these gellants are incapable of creating a stable dispersion of the biliquid foam when the aqueous phase to be gelled contains even low levels(e.g., 0.5%) of electrolytes, or salts of desired active ingredients, such as lactic acid, at an acidic pH. Unexpectedly, however, and unlike other gellants, the sulfonic acid polymer creates a homogeneous gel that is stable at a pH below 7, and applies to the skin in a smooth, aesthetically elegant manner, with no pilling, even in the presence of substantial quantities of electrolytes, e.g., 3% or more. This therefore permits the incorporation of substantial quantities of electrolytic (acidic) actives which otherwise would be impossible to use in this type of product.

The aqueous, electrolyte-containing compositions of the invention are prepared substantially in accordance with known methods for preparing aqueous gels. The amount of gellant used will depend upon the ultimate texture desired for the final product; generally, however, the gellant is added in an amount of about 0.1 to about 10% by weight of the aqueous base. The water-soluble components, including electrolytes, are added to the aqueous base containing the gellant and mixed thoroughly.

As noted above, a particularly preferred embodiment of the invention is the electrolyte-containing aqueous gel, gelled by AMPS/VIFA copolymer, containing a biliquid foam dispersed therein. Such products are prepared generally as disclosed in WO 97/32559. The typical components of a biliquid foam are water, oil and one or more surfactants, the latter being present in relatively small quantities. The aqueous phase may be any cosmetically acceptable water based material, such as deionized water, or a floral water, and will constitute from about 5 to about 50%, preferably about 10 to about 20%, by weight of the foam composition. The oil phase of the foam can be composed of any type of oil, but is preferably composed of one or more oils that are liquid at room temperature. For example, suitable oils include, but are not limited to, both cyclic and linear silicones, such as cyclomethicones; straight or branched chain volatile hydrocarbons having from 8-20 carbon atoms, such as decane, dodecane, tridecane, tetradecane, and C8-20 isoparaffins; vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum. The oil portion will ordinarily constitute from about 50 to about 90% by weight of the foam, more preferably about 70-90% by weight of the foam.

The surfactant used in the foam, or in the formulation generally can be any type of surfactant, e.g., a cationic surfactant such as quaternary ammonium compounds, sulfonium salts or an amidoamine; an amphoteric surfactant, such as an acyl amino acid, an N-alkylbetaine, an alkylimidazoline, an N-substituted alkylamine, an N-alkyl-β-aminopropionate or a sulfobetaine; an anionic surfactant, such as an acyl-lactate, an N-acylsarcosinate, an alkyl-carboxylate, an alkyl ether carboxylate, an N-alkyl glutamate, a fatty acid-peptide condensate, a phosphated ethoxylated alcohol, an alkyl sulfate, an ethoxylated alkyl sulfate, alpha-olefin sulfonate, or ester-linked sulfonate; or a nonionic surfactant, such as an alkanolamide, an amine oxide, a polyhydric alcohol ester, a polyoxyethylene or polyoxypropylene derivative of an alcohol, amide or ester, or a polyoxyethylene/polyoxypropylene block copolymer. A mixture of surfactants can also be employed. In the foam, the amount of surfactant is preferably no more than about 1%, by weight of the oil phase of the foam.

Biliquid foam can be prepared, for example, by blowing air through the water base and the water soluble surfactant used in the aqueous phase, to create a foam; the oil phase, including any additional surfactants and other lipophilic materials to be used, and then added to the water phase with gentle stirring. The biliquid foam is then added to and dispersed in the electrolyte-containing aqueous base that has been gelled with a polymeric sulfonic acid. Ordinarily, the amount of foam in the dispersion as a whole will be about 30 to about 70% by weight, more preferably about 50 to about 65%, and the gelled aqueous phase, including additional water soluble components, will be about 70 to about 30% by weight, more preferably about 35 to about 50%.

The composition can also comprise other typical cosmetic ingredients. For example, the formulation can also contain preservatives, emollients, antioxidants, colorants, humectants, fragrance and the like, the choice being dependent upon the intended use of the product. The compositions of the invention can be used for a variety of purposes. They may form the base of a colored cosmetic product, for example, a foundation, blush, eyeshadow, to eyeliner. It may also be used in hair care products, such as shampoos, conditioners, and the like. In a preferred embodiment, the composition is used in a skin care product, such as cleansers, conditioners, moisturizers, anti-aging formulations, and the like, in which the delivery of electrolytic actives may be important. In this regard, the compositions may be used for delivery not only of cosmetic actives, such as exfoliation agents, anti-acne agents, antiperspirants, skin lightening agents and depigmenting agents, or self-tanning agents but also for pharmaceutical actives intended for topical use, such as antibiotics, wound-healing agents, antipsoriatic agents, antiviral agents, antioxidants, analgesics, anesthetics, antidandruff agents, antidermatitis agents, antipruritic agents, anti-inflammatory agents, antihyperkeratolytic agents, antipsoriatic agents, antiseborrheic agents, antihistamine agents, or vitamins.

The invention is further illustrated by the following non-limiting examples.

EXAMPLES

This example illustrates the preparation of a skin-care product according the invention:

| Material | Weight percent |
| --- | --- |
| Phase I | |
| Deionized water | QS |
| AMPS/VIFA copolymer | 2.00 |
| Phase II | |
| Magnesium ascorbyl phosphate | 0.01 |
| Titanium dioxide | 0.01 |
| Lactic acid | 4.00 |
| N-Acetyl glucosamine | 1.00 |
| Green tea extract | 0.10 |
| Caffeine | 0.10 |
| Phase III | |

-continued

| Material | Weight percent |
| --- | --- |
| Sodium hydroxide(30%) | 0.50 |
| Phase IV | |
| Grapefruit extract | 0.06 |
| Lavender Oil | 0.04 |
| Phase V | |
| Vitamin E | 0.20 |
| Phase VI | |
| Isoprene glycol | 0.50 |
| Clary sage extract | 0.05 |
| Phase VII | |
| *Biliquid foam | 60.00 |

Phase II components are combined in the main vessel, and propeller mixed. When homogeneous, Phase III is added. Phase I materials are combined with a sweep mixer, and when gelled and clear, they are added to the main vessel. Phases IV and V are added to the main vessel under homo mixing. Phase VI materials are combined and heated to 80° C., then cooled to 60° C. and added to the main vessel under homo mixing. When Phases I-VI are homogeneous, they are removed from the homomixer and place under a sweep mixer. The biliquid foam is added under sweep mixing. When this mixing is complete, the mixture is quickly again placed under the homomixer to polish.
*Biliquid foam prepared as described in WO 97/32559:

| Material | Weight percent |
| --- | --- |
| Phase I | |
| Deionized water | QS |
| Sodium hyaluronate | 0.50 |
| Polysorbate 20 | 0.80 |
| Preservative | 0.20 |
| Phase II | |
| Cyclomethicone/dimethicone/polysilicone 11/ glycyrrhetinic acid | 1.70 |
| Cyclomethicone/dimethicone/polysilicone 11/ Barley extract/wheat germ extract/linoleic acid/ Cholesterol | 69.00 |
| Phase III | |
| Squalane | 3.25 |
| Cyclomethicone/dimethicone/phenyltrimethicone/ Modified polysaccharides/polyethylene | 10.00 |

What we claim is:

1. A cosmetic or pharmaceutical composition comprising an oil-containing biliquid foam dispersed in a salt-containing aqueous phase, the aqueous phase comprising a polymeric sulfonic acid gellant which is ammonium poly(acryldimethyltauramide-co-vinylformamide) and having a pH of less than 7, the salt contained in the aqueous phase being present in the composition in an amount in the range of from about 1 about 10 percent, the gellant being present in the composition in an amount in the range of from about 0.01 to about 10 percent, and the composition comprising less than about 1 percent surfactant, wherein said weights are by weight of the total composition.

2. The composition of claim 1 in which the oil-containing biliquid foam comprises at least one oil, water and the at least one surfactant.

3. The composition of claim 1 in which the salt is derived from an alpha- or beta-hydroxy acid.

4. The composition of claim 3 in which the acid is selected from the group consisting of lactic acid, malic acid, glycolic acid, citric acid, tartaric acid, and salicylic acid.

5. The composition of claim 1 in which the gellant is present in an amount of about 1 to about 10% by weight of the total composition.

6. The composition of claim 5 in which the gellant is present in an amount of about 1 to about 5% by weight of the total composition.

7. The composition of claim 1 in which the biliquid foam contains a silicone oil.

8. The composition of claim 1 in which the oil portion of the biliquid foam is present in an amount of from about 50 to about 90% by weight of the foam.

9. The composition of claim 1 in which the biliquid foam comprises from about 30% to about 70% by weight of the total composition.

10. A cosmetic or pharmaceutical composition comprising a silicone-oil containing biliquid foam dispersed in a salt-containing aqueous phase, the aqueous phase having a pH of less than 7 and comprising an ammonium poly(acryldimethyltauramide-co-vinylformamide) gellant; the salt contained in the aqueous phase being present in the composition in an amount in the range of from about 1 to about 10 percent, the gellant being present in the composition in an amount in the range of from about 0.01 to about 10 percent, and the composition comprising less than about 1 percent surfactant, wherein said weights are by weight of the total composition.

11. The composition of claim 10 in which the biliquid foam comprises at least one silicone oil, water, and the at least one surfactant.

12. The composition of claim 10 in which the biliquid foam is present in an amount of from about 30 to about 70% by weight of the total composition.

13. The composition of claim 10 in which the oil phase of the foam comprises from about 50 to about 90% by weight of the foam.

14. The composition of claim 10 in which the salt is derived from an alpha or beta hydroxy acid.

15. The composition of claim 10 in which the gellant is present in an amount of from about 1 to about 10% by weight of the total composition.

16. A method of thickening a composition comprising biliquid foam dispersed in a salt-containing aqueous phase having a pH less than 7, comprising gelling the aqueous phase with a polymeric sulfonic acid gellant which is ammonium poly(acryldimethyltauramide-co-vinylformamide); the salt contained in the aqueous phase being present in the composition in an amount in the range of from about 1 to about 10 percent, the gellant being present in the composition in an amount in the range of from about 0.01 to about 10 percent, and the composition comprising less than about 1 percent surfactant, wherein said weights are by weight of the total composition.

17. The composition of claim 16 in which the gellant is present in an amount of from about 1 to about 10% by weight of the total composition.

* * * * *